US00PP26538P3

(12) United States Plant Patent
Schell

(10) Patent No.: US PP26,538 P3
(45) Date of Patent: Mar. 29, 2016

(54) APPLE TREE NAMED 'HS RED'

(50) Latin Name: *Malus domestica*
Varietal Denomination: HS RED

(71) Applicant: Harold E. Schell, Chelan, WA (US)

(72) Inventor: Harold E. Schell, Chelan, WA (US)

( * ) Notice: Subject to any disclaimer, the term of this patent is extended or adjusted under 35 U.S.C. 154(b) by 114 days.

(21) Appl. No.: 13/999,337

(22) Filed: Feb. 12, 2014

(65) Prior Publication Data

US 2015/0230371 P1 Aug. 13, 2015

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Susan McCormick Ewoldt
(74) *Attorney, Agent, or Firm* — Randall Danskin PS

(57) ABSTRACT

A new and distinct variety of apple tree is described, and which is characterized as to novelty by producing an attractively colored apple, which is mature for harvesting and shipment on October 2 through October 5, under the ecological conditions prevailing in Chelan County, Wash.

5 Drawing Sheets

Latin name: *Malus domestica.*
Varietal denomination: 'HS RED'.

BACKGROUND OF THE NEW VARIETY

The present invention relates to a new, novel, and distinct variety of apple tree which is denominated varietally, as 'HS RED', hereinafter.

ORIGIN

The present variety of apple tree was discovered in June 1998 as a chance limb sport then growing on an 'Oregon Spur II' apple tree (U.S. Plant Pat. No. 4,839). This 'Oregon Spur II' apple tree was growing on seedling rootstock, within the cultivated area of a commercial orchard which is located at 80 McNeil Canyon Road, Orondo, Wash. The 'Oregon Spur II' tree upon which the limb sport was discovered was first planted during the 1984 growing season. After discovery, bud wood from the promising limb sport was removed, and then T-budded into a two year old 'Oregon spur II' apple tree, which was then growing on M106 rootstock (unpatented) during August 1998. This first asexual reproduction of the variety occurred at a commercial orchard, which is located at 452 Godfrey Springs Lane, Chelan County, Chelan, Wash. The aforementioned orchard is located in USDA Zone 7A. Fruit generated from this first asexually reproduced tree was identical in appearance and development as that expressed by the originally discovered sport limb. Further, additional asexually reproduced trees were propagated from the wood gathered from this first asexually reproduced tree and which were later grafted onto M106 rootstock. The subsequently planted, and asexually reproduced trees were then grown in the same orchard, which is located in Chelan, Wash. This propagation took place during the 2006 growing season. Fruit produced from the subsequent generations of trees have been found to be identical to that of the original discovered sport limb.

SUMMARY OF THE NEW VARIETY

'HS RED' appears to be a whole tree bud mutation of the 'Oregon Spur II' Red Delicious apple tree [U.S. Plant Pat. No. 4,839]. However, the newly discovered tree differs from its parent by its fruit characteristics, and further in its spur development, and blooming dates. 'HS RED' exhibits a more intense spur development resulting in a more compact tree form than that which is typically seen with the 'Oregon Spur II' apple tree when it is grown on M106 rootstock [unpatented]. More specifically, the fruit of the 'HS RED' exhibits a conical fruit form, which is so characteristic of the fruit produced by the 'Oregon Spur II' apple tree, but its skin appearance, flesh color, flesh vascular bundle color, and harvest fruit characteristics, as set forth below, are quite different. In particular, the skin color development of the 'HS RED' is fully and uniformly developed as a wash-type color three months prior to the harvest, in relative comparison to the fruit produced by the 'Oregon Spur II' apple tree, which is just beginning to develop its stripe colored pattern at that time. In regards to the new variety, it has been noted that as the skin color is developing, so is the corresponding flesh color developing to its final harvest color. In contrast, the fruit produced by the 'Oregon Spur II' apple tree does not develop its final flesh color until it is very close to full harvest maturity. It should also be noted that all the vascular bundles surrounding the core area of the fruit are colored in the 'HS RED' apple tree, and appear as hues of its skin color. In contrast, the bundles as seen in the fruit produced by the 'Oregon Spur II' fruit are not so colored. Moreover, the sugars; acid levels; pH; brix; and fruit pressures are different in the new variety's fruit at full harvest maturity when compared with the closest known variety. In particular, the fruit of the 'HS RED' apple tree displays a higher pressure; a higher brix; a higher acid level; and lower pH than that which is typically seen in the fruit produced by the 'Oregon Spur II' apple tree, when grown under similar conditions. It should be noted that these differences are not typically observed following four months in common storage at the same geographical location. The date of full bloom of the 'HS RED' apple tree is noted to be three days in advance of the 'Oregon Spur II' apple tree when grown at the same geographical location.

BRIEF DESCRIPTION OF THE DRAWINGS

The accompanying drawings, which are provided, are color photographs of the new apple variety.

Figure 1:
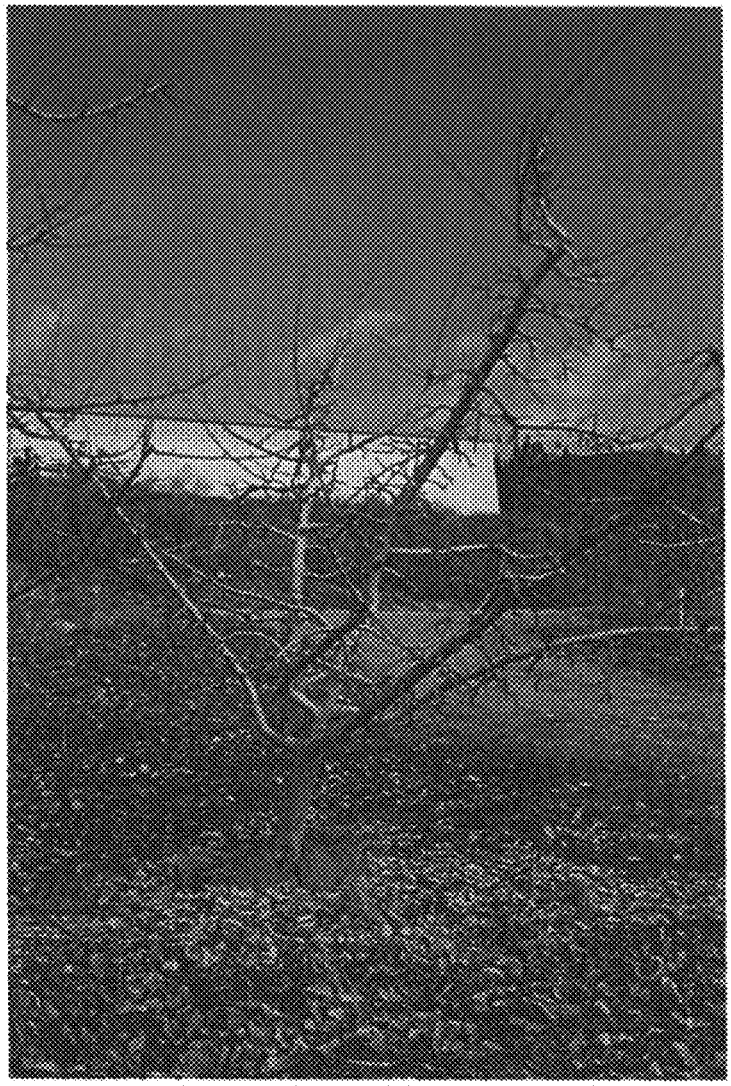
FIG. 1 depicts an 'HS RED' tree when the tree is at full dormancy.
Figure 2:
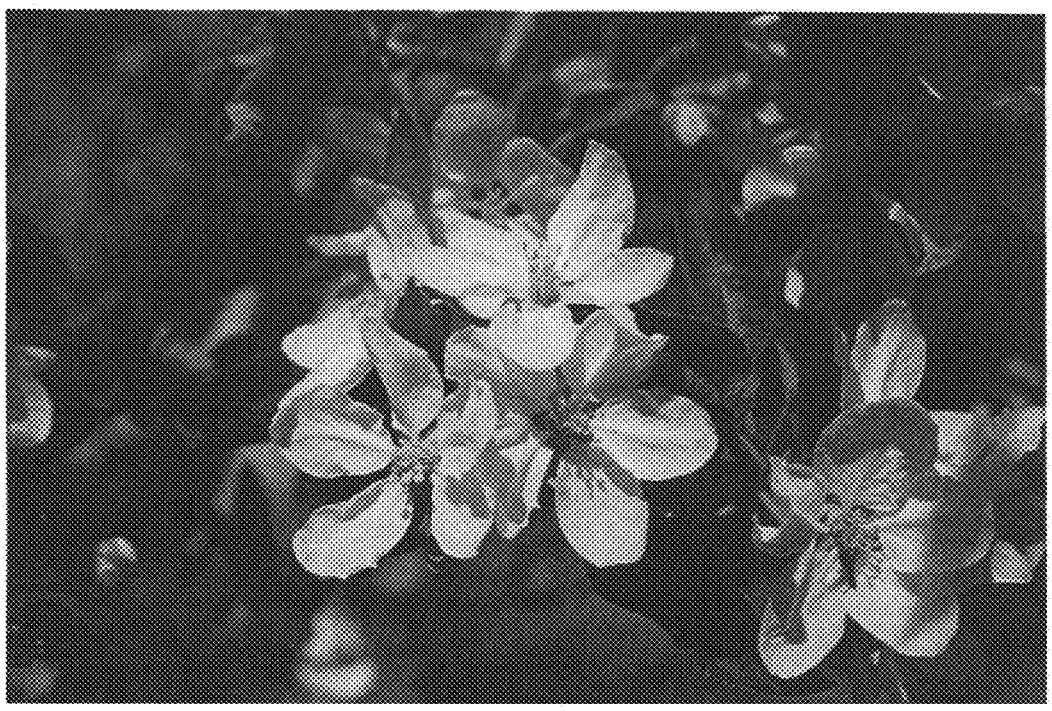
FIG. 2 is a view of the blossoms produced by the 'HS RED' apple tree at full bloom.
Figure 3:
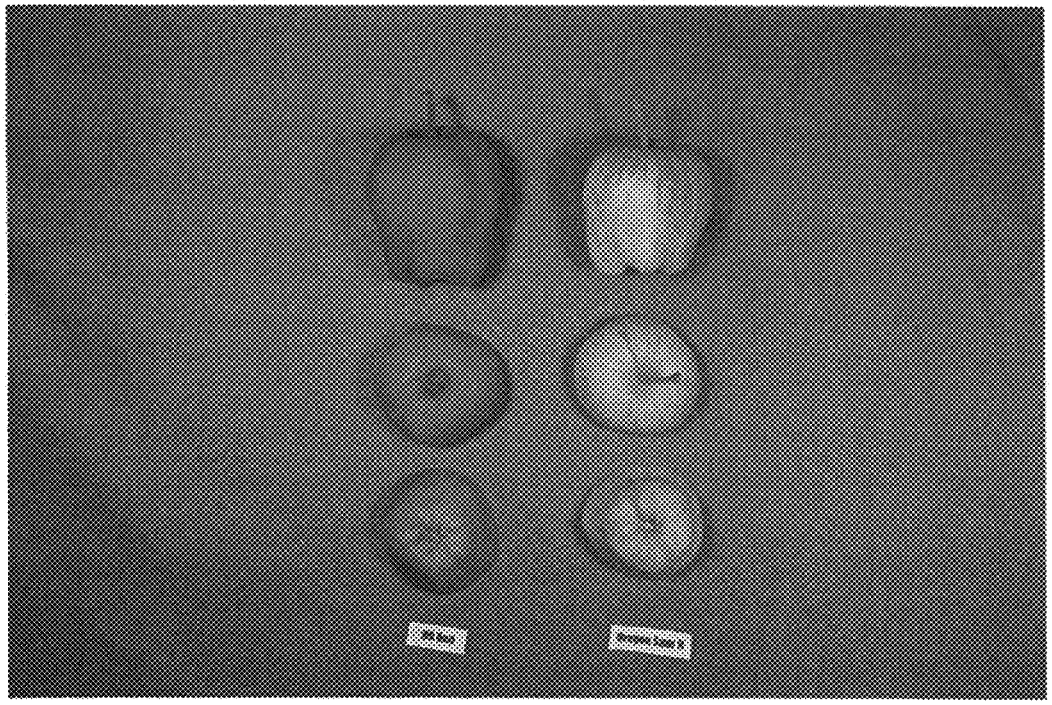
FIG. 3 shows the immature fruit produced by the 'HS RED' apple tree as compared with the fruit produced by the 'Oregon Spur II' apple tree early in their respective color development.
Figure 4:
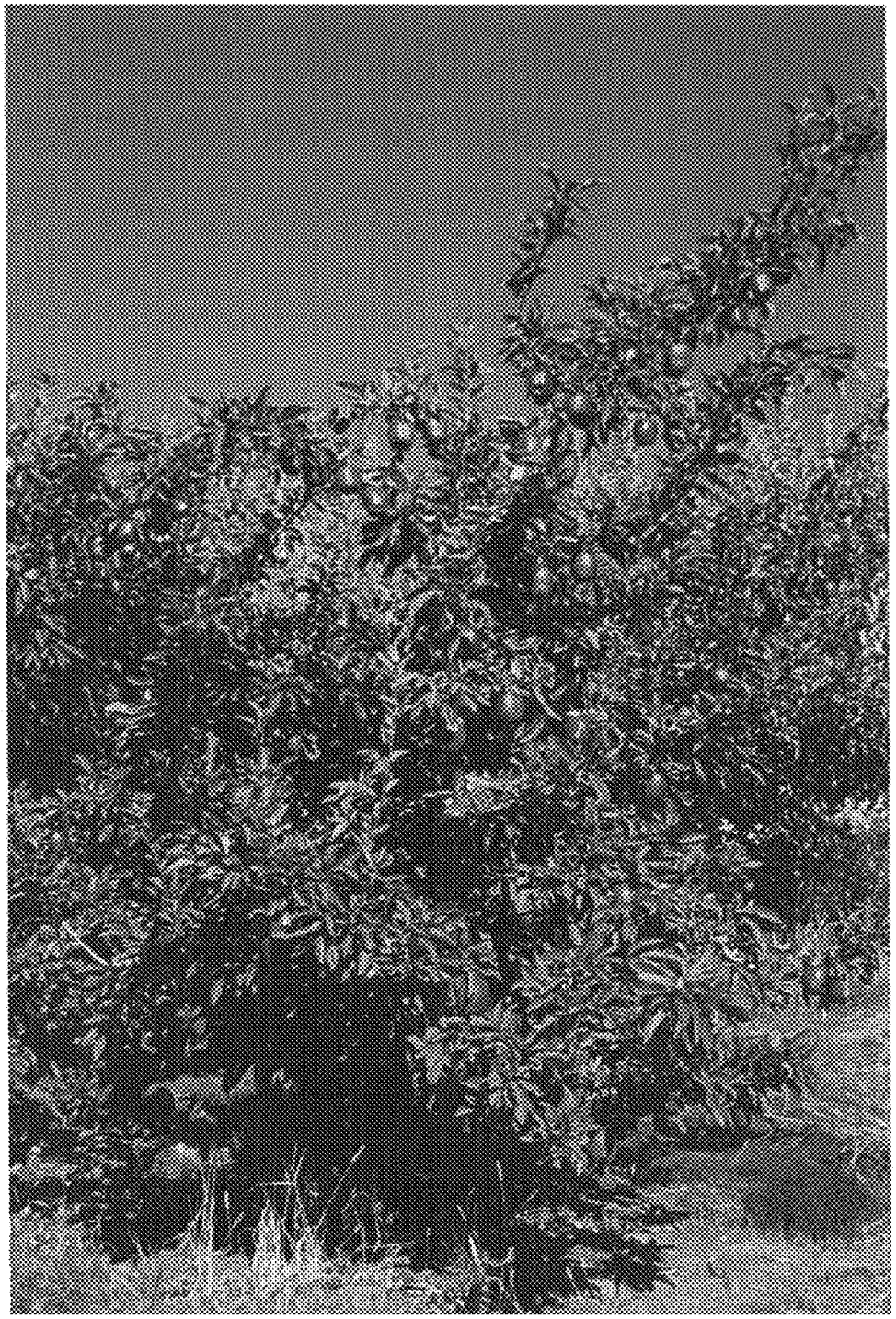
FIG. 4 depicts an 'HS RED' apple tree at full harvest maturity.
Figure 5:
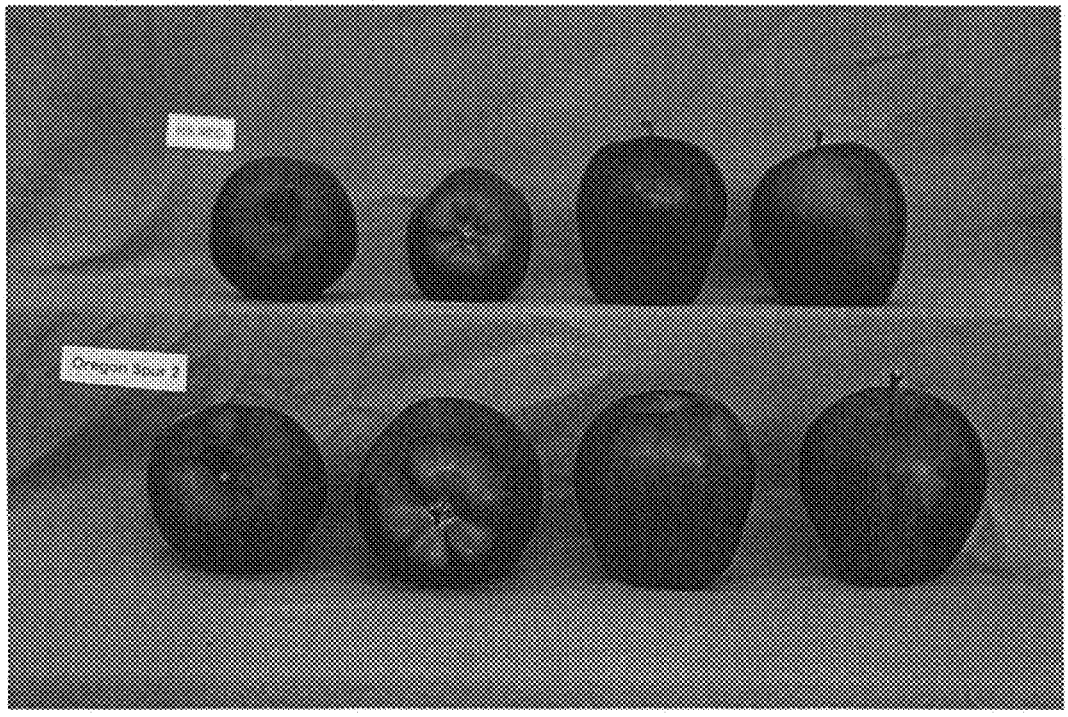
FIG. 5 depicts the mature fruit harvested from the 'HS RED' apple tree as compared to the fruit produced by the 'Oregon Spur II' apple tree at full color development.

The colors in these photographs are as nearly true as is reasonably possible in a color representation of this type. Due to chemical development, processing and printing, the leaves and fruit depicted in these photographs may or may not be accurate when compared to the actual specimen. For this reason, future color references should be made to the color plates [Royal Horticultural Society Colour Chart], and the color descriptions as provided hereinafter.

NOT A COMMERCIAL WARRANTY

The following detailed descriptions are prepared solely to comply with the provisions of 35 U.S.C. §112, and does not constitute a commercial warranty [either expressed or implied], that the present variety will, in the future, display the botanical, pomological or other characteristics as set forth, hereinafter. Therefore, this disclosure may not be relied upon to support any future legal claims, including, but not limited to, breach of warranty and merchantability, or fitness for any particular purpose, or non-infringement which is directed in whole, or in part to the present variety.

DETAILED DESCRIPTION

Referring more specifically to the pomological details of this new and distinct variety of apple tree, the following has been observed on third generation trees which are in their third leaf, and under the ecological conditions prevailing at a commercial orchard, which is located near Chelan, Wash. All major color code designations are by reference to The R.H.S. Colour Chart [4$^{th}$ Edition], and which is provided by The Royal Horticultural Society of Great Britain. Common color names are also occasionally used.

TREE

Tree type:
- *Generally*.—Considered to be a spur-type tree, which exhibits tip bearing. The current trees were grown, and are trained to a central leader arrangement.

Regularly bearing: The present variety is considered to be a consistent bearer with heavy spur development.

Vigor: The vigor of the present variety of apple tree is considered to be in the low to moderate range.

Overall shape: Considered upright, and spreading, when trained to a central leader system.

Tree height: About 17 feet.

Tree width: About 18 feet.

Tree hardiness: Considered hardy for the region in which it is currently grown.

Productivity: Preliminary observations of the small number of trees which are currently in existence indicates that the new tree will probably have a productivity which is quite high for the species. However, an accurate measurement of the tree productivity currently cannot be made.

Trunk:
- *Size*.—The present variety has a trunk diameter of about 30 cm when measured at a height of about 33 cm above the graft union.

Trunk:
- *Bark texture*.—Approximately 80% of the bark is considered to be smooth with the remainder portion of the bark having a rough texture.

Trunk:
- *Bark color*.—Gray/brown [RHS Group 199B].

Bark lenticels:
- *Generally*.—Present and moderate in number, and averaging about 8 lenticels per 4 cm$^2$.
- *Lenticel shape*.—The lenticel shape varies from round to elongated.
- *Lenticel size*.—The average width of the lenticels are about 1.3 mm; the average length is about 4.8 mm; and the average diameter is about 1.8 mm.
- *Lenticel color*.—Brown, [RHS Group 200B].

FIRST YEAR BRANCHES

First year branches:
- *Diameter*.—When measured at the midpoint of growth, the first year branches have an average diameter of about 4.3 mm.

First year branch length: About 33.7 mm.

First year branch color: Gray/orange [RHS Group 166A].

First year branch lenticels: Generally speaking, the lenticels are moderate in number, and average about 12 per running centimeter of growth.

Lenticels:
- *Shape*.—Considered round in shape, and having a size of about 0.5 to about 1 mm in diameter.

Lenticel color: White [RHS Group 155C].

First year branch pubescence: Considered short and moderate in density, and further covering 100% of the surface area.

Pubescence color: Considered white [RHS Group 155C].

First year branches internodes: Generally speaking, the distance between the nodes range in length from about 20.3 mm to about 34.8 mm.

TWO YEAR OLD FRUITING BRANCHES

Branch diameter: When measured at the midpoint of growth, second year old fruiting branches have an average diameter of about 6.2 mm.

Bark color: Two year old branches generally have a gray/brown color [RHS Group 200C].

Spur development:
- *Generally*.—Considered heavy. Spurs which are observed have a length of about 6.7 mm, to about 21.9 mm. Typically first year branches are tip bearing.

Lenticels:
- *Numbers*.—Considered moderate in number, and averaging about six (6) lenticels per running centimeter of length.

Lenticel shape: Considered round, and having a diameter ranging from about 0.2 to about 1.0 mm.

Lenticel color: Considered yellow/white [RHS Group 158A].

Buds:
- *Length*.—About 8.0 mm to about 9.6 mm.

Bud diameter: About 4.4 mm to about 9.6 mm.

Bud scale color: Considered purple [RHS Group 77A].

SCAFFOLD BRANCHES

Branch size: Scaffold branches range from about 41.4 mm to about 79.2 mm in diameter.

Crotch angle: Generally speaking, and as trained, the crotch angle is flat to nearly flat, that is, the crotch angle ranges from about 80° to about 90° when measured from the vertical plane.

Branch color:

*Generally*.—The color is gray/brown [RHS Group N199B].

Lenticels:

*Numbers*.—Considered numerous, and averaging about 10 lenticels per 4 square centimeter area.

Lenticel shape and size: Considered round, and ranging in size from about 1.0 mm to about 2.5 mm in diameter.

Lenticel color:

*Generally*.—The color is gray/brown [RHS Group N 167C].

LEAVES

Leaf shape: Generally speaking the leaves of the new variety are ovate in shape.

Surface texture:

*Upper surface*.—Considered leathery with some upward puckering being observed.

Surface texture:

*Lower surface*.—Considered smooth, and having protruding veins.

Surface sheen:

*Generally*.—A high sheen is seen on the upper surface.

Pubescence:

*Generally*.—The pubescence is typically observed on the lower surface only. The pubescence is considered fine, and moderate in density, and which further extends over approximately 100% of the surface area.

Pubescence color: Considered white [RHS Group 155B].

Leaf blade length: About 6.7 mm to about 9.3 cm.

Leaf width:

*Generally*.—The leaf width ranges from about 4.1 cm to about 5.5 cm.

Leaf margin:

*Shape*.—Considered serrate.

Leaf tip:

*Shape*.—Acuminate.

Leaf base:

*Shape*.—Rounded.

Leaf stipules: Generally speaking, two stipules are present on nearly all leaves.

Leaf stipule shape: Subulate.

Leaf stipule length: About 6.2 to about 11 mm.

Leaf stipule width: About 1.0 to 3.3 mm.

Leaf stipule color:

*Upper surface*.—Considered green [RHS Group 137B].

Leaf stipule color:

*Lower surface*.—Green [RHS Group 138A].

Leaf stipule pubescence: Generally speaking, the pubescence is present on 100% of the lower surface. The pubescence is light in quantity, and the pubescence color is white [RHS Group 155B].

Leaf color:

*Upper surface*.—Green [RHS Group 137A].

Leaf color:

*Lower surface*.—Yellow-green [RHS Group 147B].

Mid vein:

*Generally*.—Considered prominent, and having considerable downiness over the entire surface area.

Pubescence color: White [RHS Group 155B].

Mid vein:

*Width*.—When measured at the mid-blade, the mid-vein width averages about 1.1 mm.

Mid vein:

*Upper surface color*.—Gray/purple [RHS Group 187D].

Mid vein:

*Lower surface*.—Yellow/green [RHS Group 151 D].

Petiole:

*Length*.—About 2.4 to about 3.3 cm. A shallow groove runs the entire length of the petiole.

Petiole diameter:

*Generally*.—About 1.3 mm to about 1.8 mm.

Petiole color:

*Upper surface*.—Gray/purple [RHS Group 186D]. The sides of the petiole are green [RHS Group 138B]. The lower surface color of the petiole is gray/purple [RHS Group 185A].

Petiole pubescence:

*Generally*.—The observed pubescence is abundant, and further has a moderate density which extends over the entire length, and circumference of the petiole.

Pubescence color: White, [RHS Group 155B].

FLOWERS

Date of full bloom: Full bloom was observed on Apr. 25, 2013. The first blooms were noted on Apr. 23, 2013; and pedal fall started on Apr. 27, 2013.

Number of blossoms per bud: Between four to five, typically five.

Full bloom of the 'Oregon Spur II' apple tree: Generally speaking, the aforementioned tree was in full bloom by Apr. 28, 2013, at the same geographical location.

Flower size:

*Generally*.—Considered large in size.

*Flower diameter*.—About 49.4 to about 59.8 mm when fully opened.

Flower petal:

*Numbers*.—5.

Petal shape: Generally speaking, these are considered to be cordate in shape on the broad side, and further having a found base, and a rounded apex. The petals are generally free with an occasional bloom that is overlapping.

*Petal width*.—About 17.9 mm.

*Petal length*.—About 26.7 mm.

Petal color:

*Unopened*.—Red-purple (RHS Group 64B].

Petal color:

*Fully opened*.—White, [RHS Group N155A], and having occasional highlights which are considered a red-purple [RHS Group 64B].

Stamen:

*Numbers*.—About 19-22.

Filament:

*Length*.—About 5.3 to about 8.9 mm.

*Filament color*.—Green-white [RHS Group 157B].

Anthers:

*Shape*.—Club-like.

Anthers size: Considered average, about 1.5 mm wide, and about 2.6 mm long.
Anthers color: Yellow [RHS Group 4D].
Pollen production:
*Generally*.—Considered moderate in abundance.
*Pollen color*.—Gray-yellow [RHS Group 161A].
Pistil:
*Style*.—The style ranges in length from about 1.8 mm, to about 9.9 mm.
Pistil fusion: The pistil is fused at a distance of about 4.3 mm from the base.
*Pistil color*.—Green-yellow [RHS Group 1C].
Pistil pubescence: This typically extends from the base to the fused region, as noted, above.
*Pubescence color*.—Green-white [RHS Group 155C].
Stigma:
*Shape*.—Club shaped.
Stigma:
*Color*.—Gray-yellow [RHS Group 162D].
Sepals:
*Numbers*.—5 per blossom are typically seen.
Sepal shape:
*Generally*.—Thinly lanceolate with the tip being acuminate in shape, and the base is truncate.
*Sepal length*.—About 10.8 mm.
*Sepal width*.—About 5.5 mm.
Sepal pubescence:
*Generally*.—Considered abundant, and present on both of the upper and lower surfaces of the sepal.
*Pubescence color*.—Gray-yellow [RHS Group 157D].
Sepal color:
*Generally*.—Both the upper and lower surfaces are colored yellow-green [RHS Group 145B]. The tips of the sepals are highlighted a gray-purple color [RHS Group 187B].
Peduncle:
*Size*.—About 19.7 mm to about 31.6 mm in length.
Peduncle:
*Diameter*.—About 1.2 mm to about 1.5 mm.
Peduncle:
*Color*.—Yellow-green [RHS Group 145A]. Still further, the shaded side of the peduncle is gray-purple [RHS Group 187B].
Peduncle:
*Surface texture*.—A white downiness is present over the entire surface. The white downiness has a color of RHS Group 155C.
Thalamus depth:
*Generally*.—About 3.4 to about 4.8 mm.

FRUIT

Fruit form:
*Generally*.—Considered conical, or elongated conical. Five distinct ribs can be seen when the fruit is observed in a plane extending across the equatorial diameter of the fruit. The fruit exhibits mild lopsidedness, and further typically has five distinct crowns.
Fruit size:
*Generally*.—Considered medium-large for the species.
*Equatorial diameter of the fruit*.—About 8.7 cm.
*Axial diameter*.—About 8.2 cm.
Stem:
*Generally*.—Considered long, and medium in thickness, for the species.
Stem:
*Length*.—About 24.6 to about 30 mm.
Stem:
*Diameter*.—About 1.9 mm to about 2.6 mm.
Stem cavity:
*Width*.—About 34.1 mm.
Stem cavity:
*Shape*.—Considered mostly acute, occasionally an obtuse shape will be seen.
Stem cavity:
*Lipping*.—Not present.
Basin cavity:
*Sides*.—Considered sloping and crowned.
Basin cavity:
*Width*.—About 28.6 mm.
Basin cavity:
*Depth*.—About 11 mm.
Basin cavity:
*Shape*.—Rounded.
Basin cavity:
*Pubescence*.—Present and downy at the base with a pubescence color being white [RHS Group 155A].
Fruit eye: Considered erect and having a reflexed tip.
Calyx lobes:
*Form*.—Separated at the base.
Fruit skin:
*Appearance*.—Smooth. A washed appearance appears over about 95% to about 100% of the surface area, and lighter mottling occurs over less than about 5% of the fruit surface area.
*Wash over color*.—Gray-purple [RHS Group 187A].
*Mottled under color*.—Gray-purple [RHS Group 183B].
Fruit skin thickness:
*Generally*.—Considered thick for the species.
*Surface texture*.—Considered tough.
Skin lenticels:
*Generally*.—The lenticels are present, considered prominent, and are further sparsely distributed.
*Lenticel number*.—About 4 lenticels appear per 9 square centimeters of surface area.
*Lenticel shape*.—Small and rounded.
*Lenticel size*.—About 0.1 to about 0.3 mm.
*Lenticel color*.—Red-purple [RHS 69C].
Fruit core:
*Generally*.—The core position is considered distant.
*Core line position*.—Considered clasping.
Core shape: Cordate.
Core length: About 35.4 to about 39.1 mm.
Core diameter: About 32 mm to about 42.7 mm.
Fruit cell: Generally speaking is considered axial and open.
Cell form:
*Generally*.—Tufted. This is considered light and irregular.
Cell shape: Kidney-like.
Cell length: About 19.6 mm.
Cell depth: About 9 mm.
Tube:
*Shape*.—Cone-like.
Stamen position: Considered median.
Axis:
*Generally*.—Axile and open.
Seed numbers:
*Generally*.—1 to 2 seeds may be found, most typically 2 will be observed.
Seed shape: Considered obtuse.

Seed size:

*Length*.—About 7.2 mm.

Seed size:

*Width*.—About 4.3 mm.

Seed color: Orange [RHS Group 166A].

Fruit flesh:

*Generally*.—Considered crisp; melting; juicy and sweet.

Fruit flavor: Apple-like.

Fruit browning: This characteristic is displayed once the flesh is exposed to the ambient atmosphere for about 10 minutes.

Flesh color: White [RHS Group 155B].

Vascular bundles:

*Orientation*.—The vascular bundles surrounding the core are distinct, and further have a color of gray-purple [RHS Group 183B]. Bleeding from the skin region is not typically noted.

Flesh aroma: Earthy, apple-like.

Date of harvest maturity: October 2 to October 5, under the ecological conditions prevailing in Chelan County, Washington State.

Keeping quality: Considered good for the species. The fruit of the present variety has been kept up to four months in storage with no deleterious effects observed.

Pollination: Any diploid apple having the same bloom season may be utilized with this new variety.

Fruit use: Dessert. The present variety is considered of excellent eating quality, and which further has a snappy, juicy, sweet flavor, and further has a white flesh that is not starchy.

Disease and insect resistance: The present variety appears to be susceptible to all insects and diseases found in the central region of Washington State. The fruit of the present variety does not exhibit any physiological disorders on the tree, nor does it exhibit any other disorders during normal length storage periods.

Fruit pressure:

*Generally*.—The present variety displays a fruit pressure of about 16.1 pounds. This is in contrast to the fruit pressure displayed by the 'Oregon Spur II' Apple Tree at full harvest maturity which is about 15.2 pounds.

Brix: At harvest maturity, the present variety produces fruit having a brix of about 12.8. This is in contrast to the fruit produced by the 'Oregon Spur II' Apple Tree which at full harvest maturity displays a brix of about 11.6.

Acidity:

*Generally*.—The present variety produces an acidity of about 3.8 at full harvest maturity. This is in contrast to the fruit produced by the 'Oregon Spur II' Apple Tree, which, at full maturity produces an acidity of about 3.79.

*Acid Concentrate as measured in grams per liter*.—The present variety produces fruit having an acid concentration of about 3.17, as compared to the fruit produced by the 'Oregon Spur II' Apple Tree which, at full harvest maturity, has an acid concentration is about 2.83.

Although the new variety of apple tree possesses the described characteristics when grown under the ecological conditions prevailing in Chelan County, Wash., in the central part of Washington State, it should be understood that variations of the usual magnitude and characteristics incident to changes in growing condition, fertilization, pruning, pest control, frost, climatic variables and horticultural management practices are to be expected.

Having thus described and illustrated my new variety of apple tree, what I claim is new and desire to secure by Plant Letters Patent is:

1. A new and distinct variety of apple tree, substantially as illustrated and described, and which is characterized principally as to novelty by producing an attractively colored apple, which is mature for harvesting and shipment on October 2 through October 5, under the ecological conditions prevailing in Chelan County, Wash.

* * * * *